United States Patent
Gommel et al.

(10) Patent No.: US 12,320,546 B2
(45) Date of Patent: Jun. 3, 2025

(54) APPARATUS HAVING A PROTECTIVE ENVELOPE, USE THEREOF, AND METHOD FOR OPERATING A ROOM REGION

(71) Applicant: Fraunhofer-Gesellschaft zur Förderung der angewandten Forschung e.V., Munich (DE)

(72) Inventors: Udo Gommel, Stuttgart (DE); Frank Bürger, Stuttgart (DE); Daniel Falch, Stuttgart (DE); Miroslav Kopcok, Stuttgart (DE); Markus Keller, Stuttgart (DE); Viola Hoffmann, Stuttgart (DE)

(73) Assignee: FRAUNHOFER-GESELLSCHAFT ZUR FÖRDERUNG DER ANGEWANDTEN, FORSCHUNG E.V., Munich (DE)

( * ) Notice: Subject to any disclaimer, the term of this patent is extended or adjusted under 35 U.S.C. 154(b) by 518 days.

(21) Appl. No.: 17/795,296

(22) PCT Filed: Oct. 7, 2020

(86) PCT No.: PCT/EP2020/078107
§ 371 (c)(1),
(2) Date: Jul. 26, 2022

(87) PCT Pub. No.: WO2021/151531
PCT Pub. Date: Aug. 5, 2021

(65) Prior Publication Data
US 2023/0093603 A1 Mar. 23, 2023

(30) Foreign Application Priority Data
Jan. 28, 2020 (DE) .................... 10 2020 200 982.1
Apr. 16, 2020 (DE) .................... 10 2020 110 451.0

(51) Int. Cl.
*F24F 3/163* (2021.01)
*A61L 2/00* (2006.01)
(Continued)

(52) U.S. Cl.
CPC ............ *F24F 3/163* (2021.01); *A61L 2/0047* (2013.01); *A61L 2/10* (2013.01); *A61L 2/26* (2013.01);
(Continued)

(58) Field of Classification Search
CPC ........ F24F 3/163; F24F 3/167; F24F 13/0281; F24F 13/068; F24F 13/0218;
(Continued)

(56) References Cited

U.S. PATENT DOCUMENTS

| 3,936,984 A | 2/1976 | Yando |
|---|---|---|
| 4,581,986 A | 4/1986 | Conklin et al. |

(Continued)

FOREIGN PATENT DOCUMENTS

| DE | 2523512 A1 | 12/1975 |
|---|---|---|
| DE | 202007006121 U1 | 8/2007 |

(Continued)

OTHER PUBLICATIONS

Machine Translation of DE2523512, 14 pages.
(Continued)

*Primary Examiner* — Sean M Luck
(74) *Attorney, Agent, or Firm* — Fitch, Even, Tabin & Flannery LLP

(57) ABSTRACT

The invention is an apparatus having a protective envelope which is designed and constructed to envelope at least one room region, such that the protective envelope is able to separate the at least one room region from an environment immediately surrounding the protective envelope, and use thereof. Methods for operating a production engineering unit (Continued)

under cleanroom conditions and for creating and operating a virus-free and cross-contamination free room region surrounded by a protective envelope for accommodating persons and/or objects subject to quarantine. The invention has a protective envelope with at least two layers separated by a spacer layer, that is flow-permeable.

16 Claims, 9 Drawing Sheets

(51) Int. Cl.
    *A61L 2/10*     (2006.01)
    *A61L 2/26*     (2006.01)
    *F24F 3/167*     (2021.01)
    *F24F 13/02*     (2006.01)
    *F24F 13/068*     (2006.01)
    *A23B 2/53*     (2025.01)
    *F24F 11/00*     (2018.01)

(52) U.S. Cl.
    CPC .......... *F24F 3/167* (2021.01); *F24F 13/0281* (2013.01); *F24F 13/068* (2013.01); *A23B 2/53* (2025.01); *A23V 2002/00* (2013.01); *A61L 2202/11* (2013.01); *A61L 2202/123* (2013.01); *A61L 2202/14* (2013.01); *A61L 2202/21* (2013.01); *F24F 2011/0005* (2013.01); *F24F 13/0218* (2013.01)

(58) Field of Classification Search
    CPC ............ A61L 2/0047; A61L 2/10; A61L 2/26; A61L 2202/11; A61L 2202/123; A61L 2202/14; A61L 2202/21
    See application file for complete search history.

(56) References Cited

U.S. PATENT DOCUMENTS

| | | | |
|---|---|---|---|
| 4,904,514 A | | 2/1990 | Morrison et al. |
| 5,664,995 A | * | 9/1997 | O'Keefe ................. F24F 3/167 |
| | | | 454/60 |
| 7,189,349 B2 | * | 3/2007 | Karle ........................ A61L 2/10 |
| | | | 422/294 |
| 2010/0105309 A1 | * | 4/2010 | Ishibashi ................. F24F 8/108 |
| | | | 454/49 |
| 2012/0067215 A1 | * | 3/2012 | Lindahl ................ B01D 46/521 |
| | | | 96/153 |

FOREIGN PATENT DOCUMENTS

| | | |
|---|---|---|
| EP | 0859105 A1 | 8/1998 |
| WO | 2007102798 A1 | 9/2007 |
| WO | 2017015207 A1 | 1/2017 |

OTHER PUBLICATIONS

Machine Translation of DE20200700612, 12 pages.
International Search Report for PCT/EP2020/078107, mailed Jan. 29, 2021; 14 pages.

* cited by examiner

APPARATUS HAVING A PROTECTIVE ENVELOPE, USE THEREOF, AND METHOD FOR OPERATING A ROOM REGION

CROSS REFERENCE TO RELATED APPLICATIONS

Reference is made to PCT/EP2020/078107, filed Oct. 7, 2020, German Application No. 10 2020 200 982.1, filed Jan. 28, 2020, and German Application No. 10 2020 110 451.0, filed Apr. 16, 2020, which are incorporated herein by reference in their entirety.

BACKGROUND OF THE INVENTION

Field of the Invention

The invention relates to an apparatus having a protective envelope that is suitable and designed for enveloping at least one room region, with the result that the protective envelope capable of separating the at least one room region from an environment directly surrounding the protective envelope, and to the use thereof. Methods for operating a production engineering unit under cleanroom conditions and a virus-free and cross-contamination free room region surrounded by the protective envelope for accommodating at least one of persons and objects subject to quarantine are also described.

Description of the Prior Art

In situations where production engineering units, for example robots, manipulators, passive supporting structures or other handling mechanisms, need to be used under cleanroom conditions but do not themselves satisfy the necessary provisions regarding cleanliness. This can be managed by placing protective covers at least one of over and around the unit in question, to isolate or separate the cleanroom from the unclean unit.

A species-related protective apparatus of such kind for an industrial robot is indicated in DE 20 2007 006 121 U1, wherein for purposes of mechanical strength as well as fluid leak tightness, this apparatus provides at least two flexible protective envelope layers, one of which is made from a flexible plastic material and the other has a metal-containing layer. The flexible envelope surrounds a room region where the unit is located, through which a protective gas also flows.

WO 2017/015207 A1 describes a similar protective measure for a robot, represented as a tubular drape which can be fitted over the robot arm in a gastight manner with attachment fittings, and hermetically encloses a spatial region that contains the robot arm. Optionally, a fluid duct is positioned in or on the tubular drape, stabilizing the spatial form of the tubular drape, and through which a fluid stream passes, also serving cooling purposes.

U.S. Pat. No. 4,904,514 discloses a protective covering for mechanical handling units which may have several parts which placed in mutually overlapping manner on the handling units depending on the configuration of the unit that is to be shielded. The protective covering, which is partly of multiple layers, is made from non-textile material which is impermeable to fluids and particulates.

If they have been defined at all, requirements governing all known protective devices until now have been insufficient to ensure cleanroom and cleanliness suitability standards, with the result that they are unsuitable for use in cleanrooms or their suitability is limited.

The term "cleanroom" describes a room which is isolated from an environment, and in which the concentration of airborne particulates is kept as low as possible in keeping with the processing or activities that are to be carried out inside the room. Cleanrooms are used frequently in semiconductor production, optics and laser technology, biosciences, medical research as well as in aerospace engineering, to name just a few fields of application.

Apart from the aspect of the concentration of airborne particles or particulates, which can cause undesirable contamination of technical surfaces, especially in application areas involving chemically sensitive and also microbiologically sensitive activities, it is important to implement appropriate measures to ensure that at least one of chemical and microbiological contamination is reliably prevented inside a defined room region.

Cleanrooms are typically complex spaces with technically complicated design, to which access is gained most often through various lock systems. Cleanrooms are supplied by specially assembled air treatment systems, which ensure that contaminants in the air are removed immediately.

For the operation of a cleanroom, particle readings are taken for classification and quality testing, which enable the cleanliness of the room to be classified. Accordingly, the German industrial standard DIN EN ISO 14644-1:2016-06 provides for division into nine different cleanliness classes ISO 1 to ISO 9. Corresponding cleanroom quality requirements addressing microorganisms that are significant for food per $m^3$ of air are defined in Guideline VDI 2083. A standardized number of colony forming units (CFU) significant for pharmaceutical cleanroom applications is defined in the classification according to the EU-GMP Guideline Annex 1.

Currently known measures for enabling production engineering units or components that is, production and automation components—to be set up for use in cleanroom regions quickly and without considerable effort are unsatisfactory. Thus, at present there are no technical solutions for operating units of such kind under cleanroom conditions, since the known protection measures are not able to reliably prevent self-contamination, and furthermore only conform to insufficient cleanliness suitability criteria and mechanical properties regarding stability, tear strength, expansion behavior, electrostatic discharge capability, cleanability, and sterilizability.

Besides the problems outlined above, the most recent events associated with epidemiological viral outbreaks show that in the event of pandemics requiring precautionary measures infected persons must be separated from uninfected persons as rapidly as possible. Since the spread of virus-based diseases is often characterized by an exponential rise in the number of cases, it is imperative to make as much capacity for spatial isolation—that is quarantine—is available as possible within the shortest possible time. Due to geographical-spatial variations, it is usually not possible to reserve permanently installed quarantine regions, that is, entire hospitals. Measures must be adopted to combat the spread of diseases immediately at the points of origin, which may occur anywhere on Earth. Consequently, it must be possible to deploy systems that can be erected and installed quickly and offer effective prevention of entrained biocontamination.

Until now, this problem has not been solved satisfactorily, as in the past systems:

are most often permanently installed quarantine stations, these quarantine stations are most often not set up or available in the right regions of the world, there are not enough quarantine systems that can be transported and set up quickly.

Moreover, until now hospitals have not been able to provide quarantine rooms in sufficient numbers. If a large number of potentially infected persons are accommodated in open halls, the possibility that the infection will be passed on to the other, previously healthy individuals, is inevitable.

SUMMARY OF THE INVENTION

Underlying the invention is advancement of the development of an apparatus with a protective envelope that is designed and constructed so as to envelop at least one room region with the result that the protective envelope is able to entirely separate at least one room region from an environment directly surrounding the protective envelope, in such manner that the protective envelope satisfies the strict standards for cleanliness requirements, as defined in the German industry standard DIN EN ISO 14644-1:2016-06. The apparatus with protective envelope according to the invention is for overcoming the drawbacks associated with the related art as explained above and to enable rapid deployment at any site. For example, it should be possible to put production and automation components into service inside cleanrooms quickly and flexibly. The apparatus should also allow fast, flexible installation anywhere and offer the capability to set up virus-free and cross-contamination free regions that are suitable for at least one of safely accommodating persons and objects that are subject to quarantine.

A method is also described which ensures maintenance of a room region that is subject to cleanliness monitoring from outside the protective envelope according to the invention, and inside which a production or automation component. In short, the unit as described previously, is accommodated and operated. Additionally, a method is to be described which is a room region that can be installed quickly and inexpensively can be operated separately from the environment, serving to protect the environment from at least one of persons and objects subject to quarantine as well as to at least one of protecting persons and objects subject to quarantine from the effects of the environment.

The apparatus according to the invention has a protective envelope that envelops at least one room region, resulting in the protective envelope being able to separate the room region from an environment directly surrounding the protective envelope, in which the protective envelope has at least two layers, including a first and a second layer, which are separated by a spacer layer, and with at least the first layer being made from a material which is permeable to flows. The spacer layer has a supporting structure which spaces the two layers apart and is traversable by flow, gas flow, in a longitudinal extension of the layer, and which is preferably constructed as a spacer fabric. Further, at least one flow unit is provided which is fluidically connected to the spacer layer or to the room region that contains the unit.

In a preferred embodiment, both the first and second layers are made of a textile material, wherein the first layer has permeability to a flow rage in the range from 500 to 49,000 $m^3/m^2/h$. On the other hand, particularly for the purpose of enveloping production and automation components, the second layer is impermeable to flow, or almost completely impermeable to flow, That is it has a permeability to flow from 0 to $m^3/m^2/h$. In the event that the protective envelope is used as a quarantine measure, the second layer is also permeable to flow, but has at most the same permeability to flow as the first layer, and preferably has less permeable to flow than the first layer.

The protective envelope is placed relative to the room region so that the flow-permeable first layer is arranged closest to the room region.

The apparatus according to the solution in conjunction with a unit, for example a manipulator unit, is arranged in the room region surrounded by the protective envelope so that the unit can be operated under cleanroom conditions that exist in the environment.

Ultrapure air is delivered into the room region, for example between the protective envelope and the unit arranged inside the room region, by a flow unit, preferably in the form of a filter-ventilator unit designed and constructed to produce ultrapure air from ambient air. Alternatively, it is also possible to introduce a technical gas into the room region instead of ultrapure air. For this, the flow unit is connected to a technical gas reservoir.

The process of feeding ultrapure air or a technical gas, e.g., hydrogen peroxide ($H_2O_2$), into the room region results in the creation of a pressure differential between the room region and the spacer layer inside the protective envelope, which in turn sets up a substance flow out of the room region through the first, flow-permeable layer closest to the unit and into the spacer layer. The substance flow, carrying any at least one of particulate and molecular contaminants, is discharged from the spacer layer via a corresponding fluidic exhaust or discharge, or it is purified correspondingly. Since the second layer of the protective envelope, closest to the environment, that is the cleanroom region, is constructed to be impermeable to flow, so that no contaminants of any kind are able to pass from the spacer layer into the environment.

In combination with or alternatively to feeding ultrapure air or a technical gas into the room region between the unit and the protective envelope, a further flow unit may be used, which is fluidically connected to the spacer layer between the first and second layers and is preferably constructed as a suction unit or can be operated as a suction unit to create underpressure relative to the room region inside the spacer layer, by which a substance flow out of the room region, through the flow-permeable first layer and into the spacer layer can be initiated and initiated and maintained by the underpressure. The substance flow which is extracted through the spacer layer with the aid of the suction unit may be purified by a filter unit, which is either separated or combined with the flow unit correspondingly, and fed into the environment surrounding the cleanroom or the room region as ultrapure air. Alternatively, the extracted substance flow may be discharged through a corresponding fluid ducting system.

The protective envelope according to the invention, which in its simplest embodiment has two textile layers spaced from one another by a spacer layer and having different flow permeabilities, is preferably made from flexible, elastic, contamination-free textile material to not restrict the mobility of the production unit. Accordingly, it is also possible to construct the protective envelope according to the invention with rigid textile materials. Accordingly, it is also possible to place the protective envelope directly on the surface of the unit. In one possible embodiment, it is also possible that the first layer of the protective unit, closest to the unit, is the surface of the unit itself.

A further preferred embodiment provides a third and a fourth layer, each being separated from one another by a further spacer layer, and of which the third layer and the second layer explained previously are connected to each other by a seam or are manufactured as a single part, that is monolithically. The respective third and second layers are made from a material that is impermeable to flows, that is the layer material used for this purpose has a permeability of just 0 to 100 $m^3/m^2/h$. In contrast to this, the fourth layer is designed to be permeable to flow and has a permeability to flow in the range from 500 to 49,000 $m^3/m^2/h$. The permeability to flows of the respective first and fourth layers do not necessarily have to be identical, and they may differ from each other. Like the spacer layer in the exemplary embodiment described above, the further spacer layer also has a supporting structure which is traversable by gas in the longitudinal extension of the layer, preferably constructed as a spacer fabric. The function, arrangement relative to the unit and also the different modes of operation of the protective envelope designed according to the invention will be explained in greater detail below with reference to the drawings.

More advanced multilayer combinations are also conceivable, in which two of each of the layer systems described above, each comprising the first to the fourth layers with the two spacer layers arranged between them, are combined via one of their respective flow-permeable layers. In this way, the multilayer combinations are scalable without limit in terms of the number of their layers.

Filter-ventilator units, operable either with overpressure or underpressure, are ideally suitable for use as flow units for directing flows into the multilayer protective envelope and discharging them therefrom or into the room region that contains the production engineering unit and out of the room region, for the purpose of either controllably suctioning and collecting contaminated substance flows or in the opposite direction controllably shielding against infiltration by contaminants emanating from the unit by delivering ultrapure air into the further spacer layer situated on the respective outer side thereof.

Moreover, filter-ventilator-units are also able to produce ultrapure air by aspirating ambient air through a corresponding selection of filters.

In a further variant, the protective envelope designed according to the invention provides at least one sensor on or inside the individual layers which is able to capture state variables inside the protective envelope designed according to the invention. Sensors of the following type are suitable for this purpose: Particulate contamination (PAC), molecular or chemical contamination (MOC), temperature (T), pressure (p), humidity (h), flow, electrostatic (ESD) and biocontamination.

The sensors disposed in the respective layers or between the layers are connected electrically to enable the supply of electrical energy and transmission and receiving of signals via rigid or elastically flexible electrical conductor structures that are known per se and have little or no negative effect on the elastic properties of the protective envelope.

The signals captured with the aid of the sensors are forwarded to an evaluation and control unit, preferably located separately from the protective envelope, in which the sensor signals are evaluated in suitable form and assigned to suitable parameters. With the aid of the sensors, the detection of contamination variables, such as numbers of particles, particle size, degree of chemical contamination etc., and parameters relating to the flow conditions inside the room region containing the unit as well as inside the respective spacer layer can be determined. They can also be used to detect deformations inside the protective envelope as well as possible excessive material stresses, which may be severe enough to cause the material to fail. All detectable sensor signals are used advantageously to assure open-loop or closed-loop control of the at least one fluid flow machine, which is actively in fluidically operative communication with the protective envelope. At least one of open and closed loop control of the pressure and flow conditions prevailing in the respective spacer layers and in the room region is assured by the at least one fluid flow machine, ideally tasked primarily with assuring the function and energy-optimized maintenance of the barrier effect provided by the protective envelope.

A signal that can be generated by the open or closed-loop control unit and can be transmitted for open or closed-loop control of the at least one flow unit and to the production engineering unit for operation thereof, which may preferably be transmitted to a superordinate AI program in order to guarantee operationally optimised function monitoring and optionally also function control of the protective envelope designed according to the solution. Of course, all the sensor signals and derived parameters may also be archived in this way in a memory unit for monitoring and safeguarding quality.

In summary, the following advantages may be realized by installing at least one sensor inside the protective envelope designed according to the invention:

Ability to evaluate and predict possible wear of the production engineering unit and also of the protective envelope according to the solution, Ability to continuously monitor the integrity and functional capability of the textile protective envelope according to the solution, Ability to continuously monitor the room conditions between the protective envelope according to the solution and the production engineering unit as well as monitoring the cleanroom conditions.

Besides the above, incidents of overheating of the enveloped production engineering unit can be prevented by controlling or regulating the quantity of ultrapure air or technical gas fed into the room region.

Additionally, analyses and forecasts can be scheduled in the course of individual measuring cycles that are carried out at regular intervals with the aid of the sensors placed on the protective envelope, and these can be used to reach conclusions regarding necessary maintenance measures, and about the ageing behavior of the protective envelope designed according to the solution as well as the production engineering unit.

The protective envelope according to the invention is preferably made entirely of materials that are suitable for use in cleanrooms, thereby ensuring that no contamination of any kind can be introduced into a cleanroom area from the protective envelope.

In the same way as the protective envelope is able to maintain and guarantee the cleanroom conditions outside of the protective envelope despite the operation of a non-sterile production engineering unit which is partially or entirely surrounded by the protective envelope. The protective envelope being designed according to the invention also provides protection for the enveloped production engineering unit from harmful influence which may come from the surrounding area. For this purpose, the flow permeability of the at least first and second layers of the protective envelope designed according to the invention must be selected appropriately.

Advantageously, but not essentially, the flow permeabilities of the protective envelope designed according to the invention are uniform within the individual layers over the area extension thereof. Depending on its purpose and the production engineering unit that is to be enveloped in a given case, it may be advisable to create different flow permeabilities in directly adjacent area sections of the protective envelope. For example, it is possible to introduce textile layer areas having greater flow permeability than in neighboring sections of the protective envelope into subregions of the first layer closest to the production engineering unit. In this way, for example, flow-relevant cooling effects of different strengths may be dimensioned. The same also applies for the composition of the at least one spacer layer, in which a flow-permeable supporting structure is introduced which may be provided with different flow permeabilities in different subsections thereof.

The apparatus according to the invention is particularly suitable for at least one of creating and maintaining a room region with controlled technical cleanroom conditions inside or outside of the room region that is separated by the protective envelope.

The protective envelope designed according to the invention is particularly suitable for maintaining a room region with controlled technical cleanroom conditions outside the protective envelope, wherein a production engineering unit for use in the following industries is located inside the protective envelope: aerospace; optics; food sciences, including biochemistry, bioinformatics, biology, biomedicine, biophysics, bio- and genetic engineering, nutrition sciences, food technology, medicine, medical engineering, pharmaceuticals and pharmacology, environmental management and environmental engineering; chemistry; automotive; microsystems technology; semiconductor technology; automation technology and energy management.

The protective envelope according to the invention complements a method for operating the production engineering unit under cleanroom conditions as follows: The protective envelope must first be placed around the production engineering unit in such a way that the protective envelope separates a room region containing the unit from an environment in which cleanroom conditions exist, wherein the first layer of the protective is arranged facing the unit. Then, a relative underpressure compared to the pressure in the room region is created inside the spacer layer, with the result that a substance flow out of the room region, through the first layer and into the spacer layer forms, induced by the underpressure. Finally, the substance flow exiting the spacer layer must be discharged, and, preferably with the aid of a filter unit, converted into ultrapure air and returned to the cleanroom environment or removed appropriately.

The apparatus according to the invention is also designed to function as a device for creating a virus-free and cross-contamination free room region, which is suitable for safely accommodating at least one of persons and objects that are subject to quarantine.

For this purpose, the protective envelope is constructed in the form of a dome tent or chamber which adjoins a floor area directly, and together with the floor area delimits the room region. The protective envelope has at least two layers, a first and a second layer, which are separated by a spacer layer, wherein at least the first layer is permeable to flow, and the spacer layer has a supporting structure which keeps the two layers spaced apart and is traversable in the longitudinal extension of the layer.

At least one flow unit, preferably embodied as a filter-ventilator unit, is fluidically connected to the spacer layer and supplies the spacer layer with an air flow, preferably in the form of ultrapure air, or at least with a virus-free and biocontamination-free air supply. The virus-free and biocontamination-free air supply fed into the spacer layer passes into the room region that is delimited by the protective envelope through the flow-permeable, first layer closest to the room region. The second layer, closest to the surrounding atmosphere, is preferably also constructed to be flow-permeable, with the result that flow components dependent on the flow permeability thereof pass out of the spacer layer directly into the surrounding atmosphere.

The protective envelope also has an outlet area, through which an air flow is suctioned in a controlled manner out of the room region delimited by the protective envelope, preferably with the aid of the one or the further flow unit, which is preferably embodied as a filter-ventilator. For this purpose, the flow inlet of the one or the further flow unit is fluidically connected to the outlet area to prevent the exhaust air from passing uncontrolled from the room region into the environment. As an alternative to active aspiration of the room air with the aid of a flow unit or in combination therewith, a sterilization unit is arranged at the outlet area to ensure that room air flowing out into the environment through the outlet area is fully sterilized.

The at least one flow unit is also operable in such manner that a layer pressure $p2$ which forms inside the spacer layer is not only greater than a room internal pressure $p1$ which forms inside the room region but also greater than an ambient pressure $p3$ in the environment. This ensures that the room region surrounded by the protective envelope is perfused and flushed in controlled manner with sterile, that is virus-free and biocontamination-free air, and that no air components other than the virus-free and biocontamination-free air supply fed into the spacer layer by the flow unit preferably embodied as a filter-ventilator unit gets into the room region.

The at least one flow unit is equipped with a sterilization unit for the purpose of sterilizing supply and exhaust air. When a sterilization unit is used, the flow unit does not necessarily have to be embodied as a filter-ventilator unit, so a simple ventilator unit is sufficient. Alternatively or in combination therewith, sterilization units may be arranged along the respective flow paths between the flow outlet of the filter-ventilator unit or ventilator unit and the spacer layer and along the flow path between the outlet area and the flow inlet of the filter-ventilator unit or ventilator unit or the further filter-ventilator unit or further ventilator unit in order to produce a virus-free and biocontamination-free air supply. The sterilization unit preferably has a UVC light source capable of emitting UV light with wavelengths in the range between 220 nm and 270 nm, preferably 222 nm and 254 nm.

Besides the barrier effect described above, the apparatus according to the invention for creating a virus-free and cross-contamination free room region is also capable of imposing a cleanroom effect. The cleanroom effect may be diminished or augmented depending on the adjustable airflow rate through the spacer layer of the protective envelope and the adjustable degree of flow blockage created by the inner first and the outer second layer. This makes it possible to create quarantine shielding rooms that are almost entirely limited to the barrier effect, or which also guarantee a very pure supply to the inner area. This level is infinitely variable.

In a further preferred embodiment, sensors are implemented in at least one of the protective envelope and in the at least one flow unit in order to determine operating states and assure open- or closed-loop control of the sterile quarantine system. These sensors are preferably able to detect biocontaminants, viruses, particles or also pressure/temperature/humidity, for example.

The further preferred operating modes of the protective envelope designed according to the invention will be described in the following text with reference to the exemplary embodiments represented in the figures.

BRIEF DESCRIPTION OF THE DRAWINGS

In the following section, the invention will be described for exemplary purposes without limitation of the general inventive thought on the basis of embodiments with reference to the drawings. In the drawings.

DETAILED DESCRIPTION OF THE INVENTION

Figure 1:
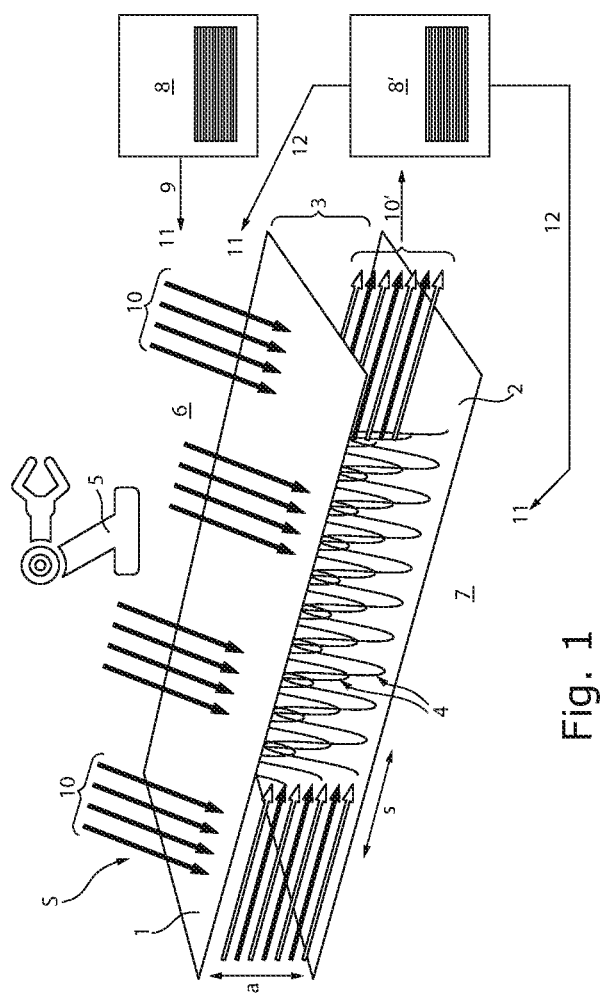
FIG. 1 is a schematic representation of a protective envelope according to the invention and illustration of the operating principle.

FIG. 1 shows a protective envelope according to the invention with a first layer 1, a second layer 2 and a spacer layer 3 which holds the first and second layers 1, 2 stable spaced at a distance a from each other. The first and second layers 1, 2 are preferably made from a cleanliness-compatible technical textile material with a permeability allowing a flow through the textile fabric which is conferred on the layers by the manufacturing process. The first layer 1 has a flow permeability preferably in a range between 500 and 49,000 $m^3/m^2/h$, whereas the second layer 2 is flow-impermeable, that is has a flow permeability in the range between 0 and 100 $m^3/m^2/h$. The spacer layer 3 has an inner supporting structure 4, preferably in a spacer fabric as a mechanical way for keeping the first and second layers 1, 2 at a distance spaced apart from each other, wherein the spacer fabric is traversable with practically no restriction over the entire longitudinal extension s of the layer.

Alternatively to the construction of the second layer 2 with a cleanliness-compatible textile material, it is also possible to use alternative cleanliness-compatible material, in the form of a plastic film, for example.

The protective envelope S according to the invention is orientated with its flow-permeable first layer 1 closest to the production engineering unit 5 and is connected thereto preferably in spatially fixed manner, with the result that the protective envelope S separates a room region 6 containing unit 5 from the environment 7 surrounding the protective envelope S, corresponding to the cleanroom, which seals it in a manner preventing transfer of fluids and contamination. The attachment of the protective layer S to the production engineering unit 5 or subsections of the production engineering unit 5 is performed using fastening mechanisms that are known per se and are not part of this invention and are known to persons ordinarily skilled in the art.

Additionally, a flow unit 8, preferably in the form of a filter-ventilator unit, which is able to produce ultrapure air 11 from ambient air, feeds the surface air into the room region 6 through a fluid duct 9. The introduction of the ultrapure air 11 into the room region 6 results in a pressure difference relative to the interior of the spacer layer 3, with the result that a substance flow 10 is created from the room region 6 and into the spacer layer 3 through the first layer 1.

The quantity of the substance flow 10 passing through the first layer 1 is dependent on the pressure differential between room region 6 and the interior of the spacer layer 3 and the selection of the flow permeability of the first layer 1.

The substance flow 10 passing through the first layer 1 comprises on one hand the supplied ultrapure air, which is contaminated with particles or the like due to the operation of the production engineering unit inside the room region 6. In addition to particulate contaminants, the substance flow may also be polluted by chemical, biological or similar contaminants, all of which pass through the first layer 1 and flow out inside the spacer layer 3 for subsequent discharge of the substance flow 10'. Since the second layer 2 presents a barrier to the incoming substance flow 10 inside the spacer layer 3, the environment 7 corresponding to the cleanroom is neither polluted nor contaminated. The substance flow 10' flowing along the longitudinal extension of the layer s can be discharged in unpressurised manner through a discharge line not shown in FIG. 1.

In a further variant, a further flow unit 8' is provided, which serves as a suction unit and is fluidically connected to the spacer layer 3. The substance flow 10' is discharged from the spacer layer 3 in controlled manner with definable suction power via the flow unit 8' which functions as a suction unit. The flow unit 8', which is also embodied as a filter-ventilator unit, is advantageously able to convert the contaminated substance flow 10' into ultrapure air 11 through corresponding filtration, and this is then returned to the environment 7, that is the cleanroom or the room region 6, via a discharge 12.

Besides the protective function of the protective envelope S according to the invention, the protective envelope S also extracts heat from or cool the production engineering unit 5 during operation thereof, since the ultrapure air fed into the room region 6 can also extract heat through the first the first layer 1 and by flowing along the spacer layer 3.

A practical alternative to feeding ultrapure air 11 into the room region 6, is the supply of a technical gas, for example $H_2O_2$, via the flow unit 8, in this case connected to a corresponding technical gas reservoir, not shown here.

Figure 2:
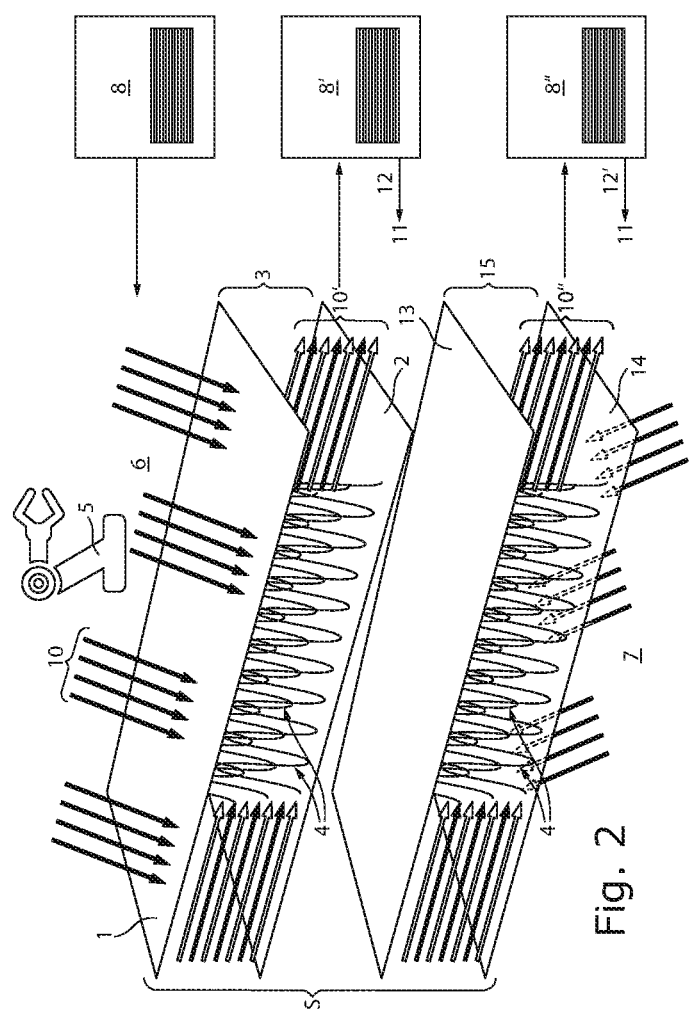
FIG. 2 is a schematic representation of a preferred embodiment for creating the protective envelope according to the invention having four layers and two spacer layers.

FIG. 2 shows an advanced embodiment of a protective envelope S according to the solution, which is a double version of the layer arrangement represented in FIG. 1. Thus, the protective envelope S of FIG. 2 has a first layer 1, a second layer 2, a third layer 13 and a fourth layer 14. To enable clearer illustration, the second layer 2 and the third layer 13 are represented as being spaced apart from one another, although they are normally connected by a join to form a single layer or as a single part of a monolithic construction. Both the first layer 1 and the fourth layer 14 are a flow-permeable textile cleanroom material, each having a flow permeability between 500 and 49,000 $m^3/m^2/h$. The second layer 2 and third layer 13 are made from flow-impermeable textile material. Like the spacer layer 3, the further spacer layer 15 enclosed between the third layer 13 and fourth layer 14 includes a supporting structure 4, keeping the third and fourth layers 13, 14 spaced from each other.

Similarly to the representation of FIG. 1, the protective envelope S is orientated with its first layer 1 closest to the production engineering unit 5, whereas the fourth layer 14 is orientated to be closest to the environment 7, corresponding to the cleanroom.

To avoid repetitions, reference is herewith made to the preceding notes regarding the operating principle of flow units 8 and 8' in terms of producing and feeding ultrapure air 11 into the room region 6 and the extraction of the contaminated substance flow 10' by controlled underpressure with the aid of flow unit 8' and optional treatment to obtain ultrapure air 11.

A further flow unit 8" is fluidically connected to the further spacer layer 15, which is delimited by the third and fourth layers 13, 14, and is operated as an underpressure source and is able to extract a substance flow 10" by suction and optionally convert it into ultrapure air 11, which can then be fed to the environment 7 via a discharge 12'. Air L is sucked out of the environment 7 through the fourth layer 14 and into the further spacer layer 15 with the flow unit 8" functioning as the underpressure source. In this way, the environment 7, which corresponds to the cleanroom, undergoes an additional purification effect.

Figure 3:
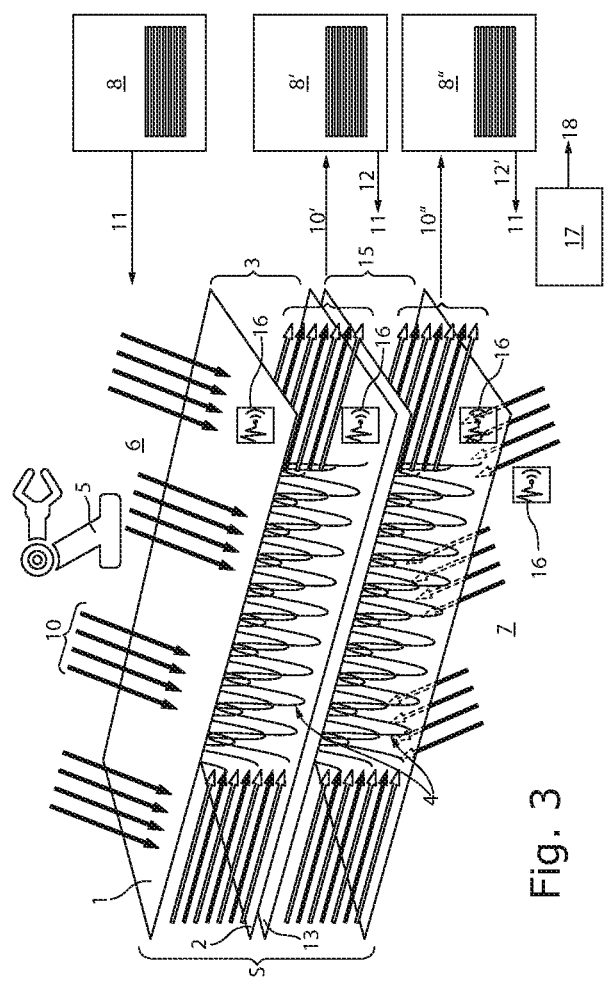
FIG. 3 is a schematic representation of a protective envelope with a sensor system.

FIG. 3 shows a protective envelope S according to the variant represented in FIG. 2, to which at least one sensor 16 has been added by mounting on or inside the protective envelope S. The number of sensors 16 illustrated in FIG. 3 and their locations for attachment on or in the protective envelope S illustrate preferred options, which however do not limit the general inventive thought. The sensors 16 mounted on or in the individual layers 1, 2, 3, 13, 14, 15 may be selected freely from the following sensor types depending on requirements: Sensor for particulate contamination (PRC), sensor for molecular or chemical contamination (MOC), temperature sensor (T), pressure sensor (p), humidity sensor (h), flow sensor, electrostatic sensor (ESD), sensor for biocontaminants, etc.

The sensors 16 which are attached to the protective envelope S can be used to capture more than contamination parameters to also detect and monitor the status of the protective envelope S, the cleanroom quality of the environment 7 as well as the operating state of the production engineering unit 5. The sensor signals generated by the individual sensors 16 are forwarded to an evaluation and control unit 17, which generates at least a signal 18 usable for further functions: Firstly, the signal 18 is used for controlled operation of the individual flow units 8, 8', 8". The signal 18 may also control the production engineering unit 5. The signal 18 may also be used by AI software or the like for analyzing and forecasting the protection function and reliability of the protective envelope in operation.

Figure 4:
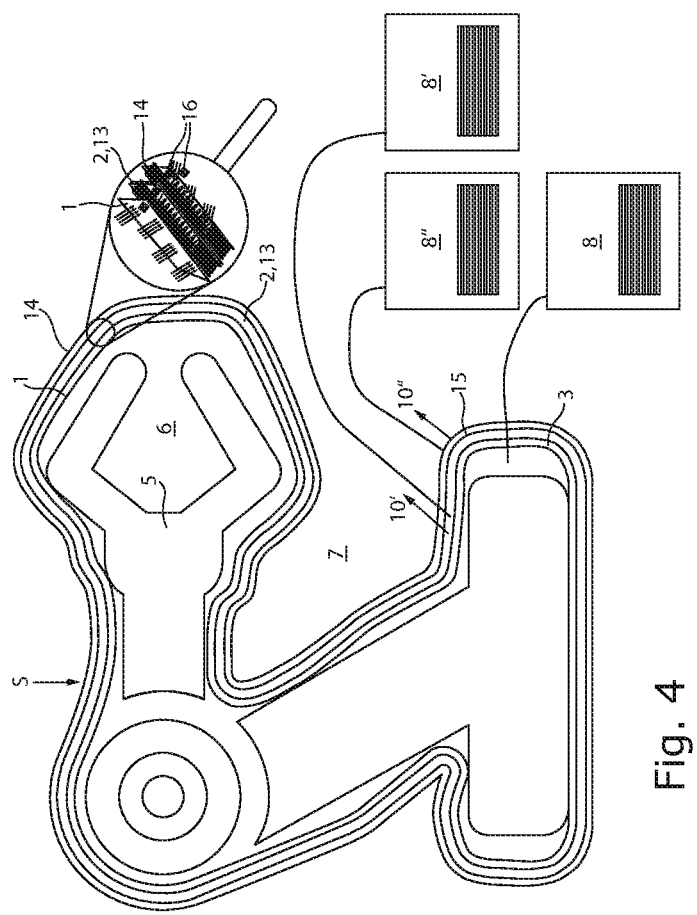
FIG. 4 is a system arrangement with protective envelope according to the invention for operating a production engineering unit.
Figure 5:
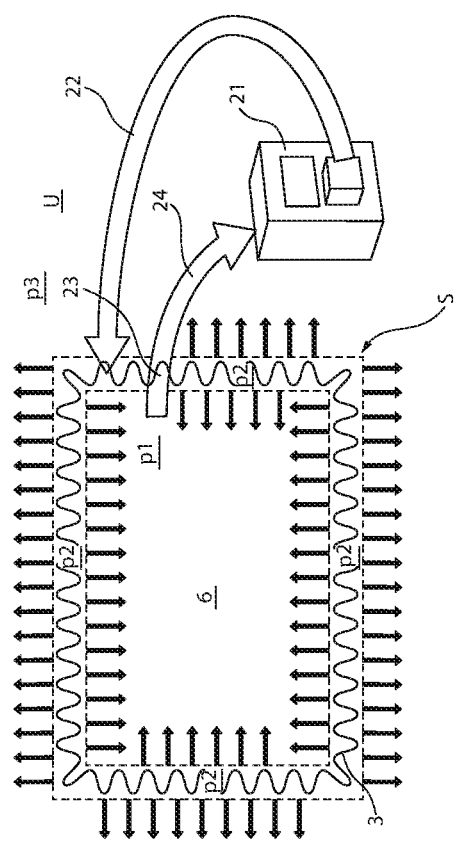
FIG. 5 is a setup of a quarantine chamber with a filter-ventilator unit.
Figure 6:
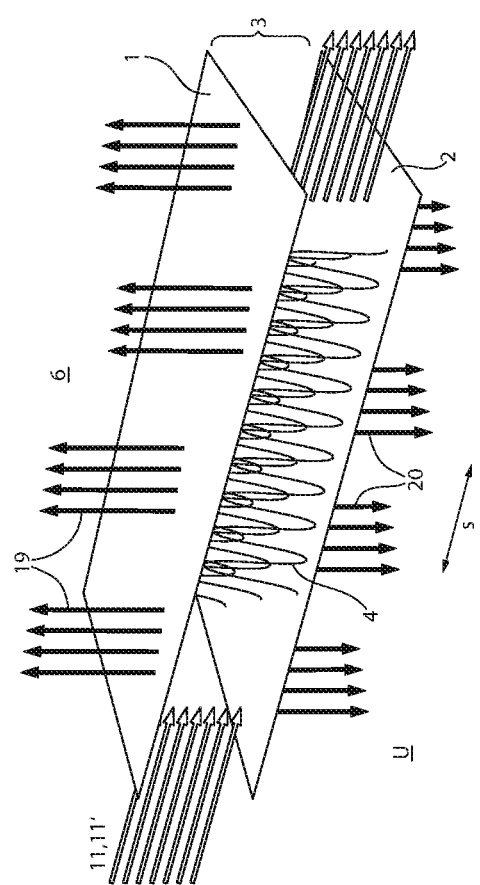
FIG. 6 is a schematic representation of a protective envelope according to the invention for a quarantine chamber and illustration of the operating principle.

FIG. 4 shows a schematic arrangement of the protective envelope S around a production engineering unit 5 to isolate from the environment 7, which preferably is a cleanroom. It may be assumed that the protective envelope S is constructed in the same manner as the variant illustrated in FIG. 3, see enlarged inset. The first layer 1 is orientated closest to the production engineering unit 5 and encloses the room region 6, while the fourth layer 14 is orientated closest to the environment 7, which is the cleanroom. The spacer layers 3 and 15 situated between them are separated by the flow-impermeable layers 2, 13.

In order to operate the protective envelope S, three flow units 8, 8', 8" are provided. The flow unit 8 feeds ultrapure air 11 or a technical gas, preferably $H_2O_2$, into the room region 6, thereby creating an overpressure with respect to the pressure conditions prevailing in the environment 7, which correspond to atmospheric pressure. The flow unit 8' is fluidically connected to the spacer layer 3 and suctions a contaminated substance flow 10' out. In the same way, the flow unit 8" which functions as a suction unit, is able to extract a substance flow 10" from the further spacer layer 15.

The protective envelope arrangement S illustrated in FIG. 4 ensures high reliability of the contamination barrier and guarantees the cleanroom condition within the environment 7 while the production engineering unit 5 is in operation.

The protective envelope S with the sensors 16 integrated therein is preferably at least one of fitted, draped and unfolded over the unit 5, for example, a robot, so that a flowing enclosure is created around the unit 5.

The apparatus according to the invention affords the following advantages in respect of cleanliness and hygiene (low level of own emissions by system elements, interior region monitored for particulates, chemical and microbiological contaminants). The flow units, in the form of a filter-ventilator unit, generate a defined volume flow in pure air qualities of air purity classes 1 to 9, as are defined in ISO 14644-1.

Variations of the defined flow management system for ensuring a defined overpressure/underpressure:

Realization by at least one cleanliness-compatible textile or multilayer covering which is constructed from at least one layer combination, that is first and second layers with the spacer layer located between them. Varying degrees of permeability of the individual layers may be chosen, depending on the cleanliness specifications that are to be satisfied.

Cleanliness conditions are provided (installation, commissioning) in a brief time window (rapid set up and teardown).

Low intrinsic rigidity, so that the motion sequence is only minimally hindered.

The apparatus for creating clean conditions is lightweight.
    Use in areas monitored for cleanliness standards.
    The apparatus satisfies the cleanliness/hygiene requirements as described in the pertinent regulation families, that is, ISO 14644, VDI 2083, cGMP classes A to D (defines limits for the number of airborne germs).
    The apparatus fulfils the capability of mechanical cleanability of the components.
    The apparatus allows layer-specific charging with technical gases, so that protection can be provided not only for the environment but also for the product and the automation unit.
    Low adhesion forces between the textile or multilayer covering and automation components.
    The flow permeability is adjustable, so that individual zones can be defined and supplied with increased volumes of ultrapure air separately, depending the degree of soiling, for example. The same applies for other application areas, and gases, that is for dissipating thermal loads or creating a protective gas atmosphere.
    The measurement processes enable a wide range of analyze, relating to the operating history, the status of the automation unit as well as the status of the system itself, thereby assuring both good reliability and system stability.
    Construction of the protective envelope material in product-specific version (with adjustable/compilable permeability): from completely closed (airtight) through semi-permeable to completely open in terms of fluid flows.

The protective envelope material, that is the material of the first to fourth layers may also possess the following additional properties:

envelope material of the textile/multilayer covering with good electrostatic dissipation properties.
low-particulate envelope material.
low outgassing envelope material.
microbicidal and sterilisable envelope material.
particle absorbing or filtering envelope material.
no additional support construction.
complete aspiration of the production plant without additional hoses; semi-integral suction.
semi-integral suction inner side of the protective envelope (facing towards the plant/automation component) and outer side of the protective envelope are sucked into the interior of the spacer fabric together.
textile/multilayer covering (spacer material) functions as integral suction
internal air-permeable construction of the axis of rotation for underpressure suction.
close-fitting textile/multilayer covering, low bulk with minimal movement restriction.
electrically conductive.
fire-retardant.

The materials listed above are suitable for use in a protective envelope and promote rapid erection of a temporary or permanent installation for creating a virus-free and cross-contamination free room region for accommodating at least one of persons and objects subject to quarantine. FIG. 5 shows a cross-section view of an autarchically functioning flow-regulating quarantine system from above. This example shows a tent-like structure made from a textile multilayer system which in the case shown is used as a quarantine system for a single person.

In the exemplary embodiment shown, the protective envelope S that delimits the room region 6 having a first layer 1, closest to the room region 6, a second layer 2 and a spacer layer 3 which keeps the two layers 1, 2 spaced from each other. FIG. 6 shows the layer structure in detail. As with the embodiments explained previously, the first and second layers 1, 2 preferably have a cleanliness-compatible textile material with a flow permeability through the textile fabric introduced by the manufacturing process. Both layers 1 and 2 have a flow permeability preferably in range between 500 and 49,000 $m^3/m^2/h$. The flow permeabilities of both layers do not necessarily have to be identical, rather they can be selected to complement each other according to needs. The first layer 1 closest to the room region 6 preferably is a technical textile material with a lower technical flow degree of permeability, and the layer 2 closest to the environment U consists of a technical textile material with a higher technical flow degree of permeability.

For the purpose of mechanical separation of the first and second layers 1, 2, the spacer layer 3 has an inner supporting structure 4, preferably in the form of a spacer fabric, which allows practically unhindered flow permeability in the longitudinal extension direction s of the layer.

Ultrapure air 11, or at least a virus-free and biocontamination-free, sterile air flow 11', is fed into the spacer layer 3. The continuous sterile feed flow into the spacer layer 3 causes the formation of an internal layer pressure p2 as a function of the selected flow permeabilities in the first and second layers 1, 2 and the continuously flowing air stream components resulting therefrom, which pass through the first layer 1 into the room region 6, see air stream component 19, and through the second layer 2 into the environment U, as air stream component 20. The flow is preferably delivered in such manner that for the layer internal pressure p2, for the room internal pressure p1 created in the room region 6, and for the ambient pressure p3, which is equivalent to the atmospheric ambient pressure which is considered usual, the following correlation is true: p2>p1 and p2>p3, and preferably p1>p3.

In the embodiment according to FIG. 5, the supply of a continuous flow is assured by a flow unit 21, a filter-ventilator unit, is conditioned to produce pressurized ultra-pure air or at least sterile virus-free and biocontamination free supply air and deliver this into the spacer layer 3 via a sterile feed line 22. The pressurization load on the spacer layer 3 in the protective envelope S originating from the flow unit 21 as well as the make-up of the protective envelope S itself are preferably chosen such that at least one of the tent and chamber-like quarantine protection apparatus is self-erecting and forms a self-supporting, dimensionally stable structure solely under the effects of the overpressure p2 created in the spacer layer 3. Of course, known bearing, at least one of supporting and suspension measures for the protective envelope S may also be used as needed to assure a dimensionally stable arrangement and deployment of the quarantine protection apparatus. Thus for example the static-mechanical construction and rigidity of the quarantine protection apparatus, may alternatively be realized by the following structural variants:

a bearing and supporting external scaffold/pole assembly or framework to which the textile protective envelope or parts thereof are fastened,
a self-supporting textile protective envelope, parts or all of which gain their rigidity from the applied internal pressure, which is greater than the ambient pressure of the surrounding atmosphere,
a self-supporting textile multilayer envelope, parts or all of which are intrinsically rigid and are therefore self-supporting.

In order to guarantee that the environment U does not become contaminated by the quarantine protection apparatus, the protective envelope S has a defined outlet area 23 which is fluidically connected to a discharge 24 that leads to the flow unit 21. In the flow unit 21, the exhaust air exiting the room region 6 is sterilized, and after sterilization is returned to the feed line 22 in a closed circuit, for example, or discharged into the environment U. Depending on the conditions on-site, in this way it is possible to operate the quarantine protection apparatus in complete isolation from the environment U with a "closed-loop air flow", or after complete sterilization the ambient air can be used, in which case, after the room region 6 has been uniformly filled with sterile air the contaminated air may be discharged into the environment U following corresponding sterilization.

Because it entails the use of so few materials and components, the protection apparatus according to the invention can be set up and put into operation within a few minutes.

The flow-permeable textile material used for making the protective envelope designed as a multilayer system may be constructed as a flexible, elastic or even a rigid layer, for example in in the form of woven layers, film layers or plate material with defined degrees of perforation, which means that, when not filled with air even large numbers of the protection apparatuses can be stored and stockpiled and do not take up an inordinate amount of space. The flow-permeable material preferably satisfies the same cleanliness requirements to which the textile material used in the preceding embodiments in FIGS. 1 to 4 is also subject.

In order to create the pressure conditions described, that is p1<p3<p2, at least one or also several flow units may be used, working with overpressure or underpressure to either extract contaminated air in controlled manner out of the room region 6 and collect it, or conversely to isolate the contaminants from the external region.

Figure 7:
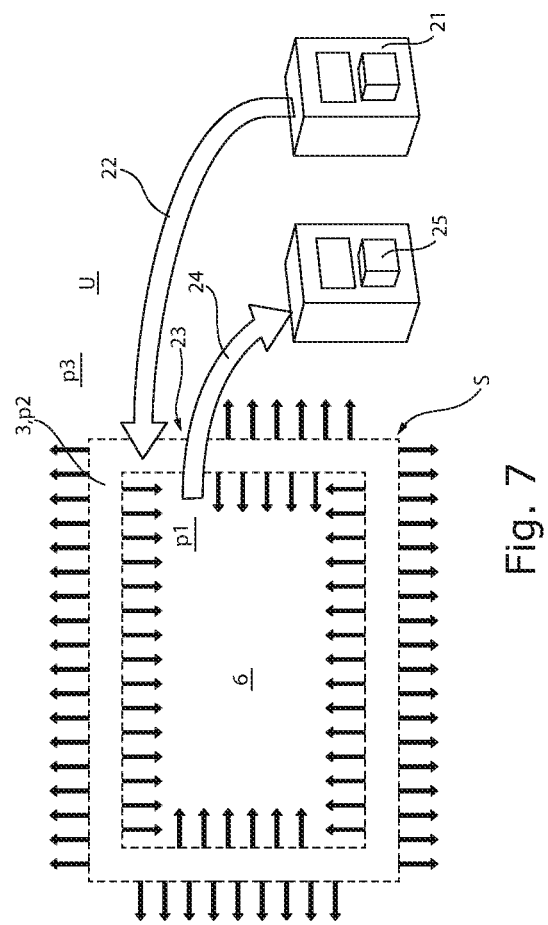
FIG. 7 is a setup of a quarantine chamber with two filter-ventilator units.

FIG. 7 shows a variant of the embodiment in which the spacer layer 3 of the protective envelope S is flooded with sterile supply air via the sterile feed line 22 from a first flow unit 21 which is embodied as a filter-ventilator unit. A second flow unit 25, preferably also embodied as a filter-ventilator unit is connected via a discharge 24, which is connected in fluid-tight manner to the outlet area 23 of the protective envelope S, to the room region 6, from which the second flow unit 25 sucks out and safely disposes of contaminated room air, that is the contaminated room air is sucked out and fully sterilized and discharged into the surrounding atmosphere.

For the purpose of sterilizing the supply air from the surrounding atmosphere or the contaminated air extracted from room region 6, besides known sterilization techniques such as gamma sterilization, H2O2 sterilization, HEPA filters or heat input using heaters, sterilization by UVC irradiation in the far UVC wavelength range at about 222 nm is particularly effective. The use of an UVC irradiation unit may be applied in many situations for the regions and components of the quarantine system according to the invention, for example as integral radiation components within a filter-ventilator unit, on the protective envelope inside the room region, on or inside the protective envelope, for example in the form of a multiplicity of LED floodlamps. UVC irradiation units of such kind may be arranged particularly at the flow outlet area or along the feed and discharge lines.

Figure 8:
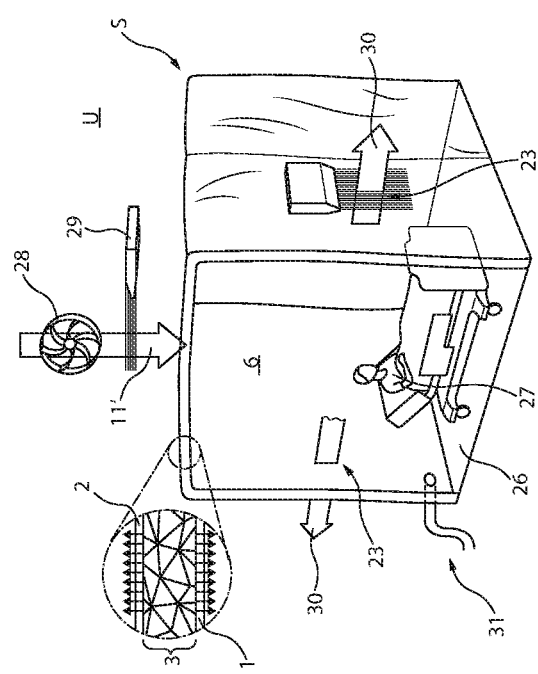
FIG. 8 is a alternative variant of a quarantine chamber.

FIG. 8 shows a preferred exemplary embodiment of a quarantine chamber, in which the protective envelope S together with a floor area 26, on which the protective envelope S is supported, forming a peripheral edge, flush and substantially gas-tight, encloses an inner room region 6, in which a person subject to quarantine 27 is accommodated. A quarantine chamber with a floor element joined permanently to the protection structure, constructed in the manner of a cloth or film for example, would also be conceivable. Sterilised supply air 11' is introduced into the spacer layer 3 of the protective envelope S through the second layer 2 closest to the environment U by a schematically represented ventilator unit 28. A UVC irradiation unit 29 ensures the necessary sterilisation of the supply air. Induced by overpressure, contaminated room air 30 passes through the outlet areas 23 provided in the protective envelope S, in each of which a further UVC irradiation unit 29' is mounted for sterilization purposes and into the environment. It is thereby ensured that as far as possible no undesirable viruses or biocontaminants are transported from the environment to the quarantined patient 27, nor from the quarantined patient 27 into the surrounding outside air.

In order to optimize the interior quarantine area, additions of technical gases 31, that is pure oxygen, may be introduced in metered quantities.

Figure 9:
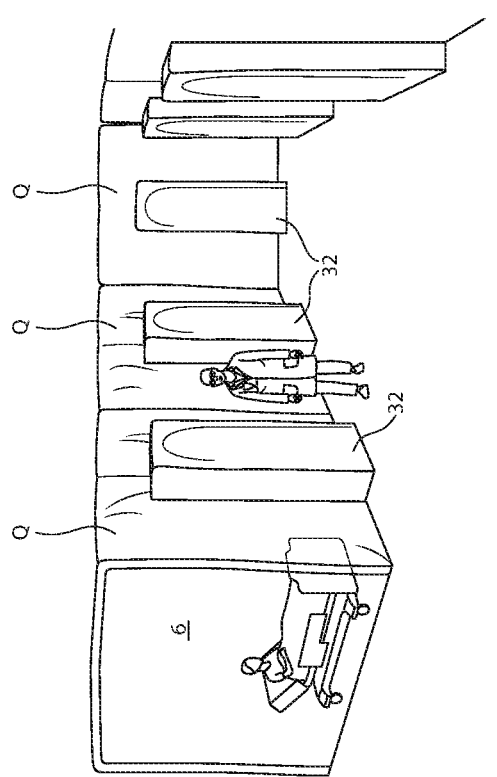
FIG. 9 is a multi-modular assembly with a single quarantine chambers.

The quarantine system illustrated in FIG. 8 serves as a modular construction unit by combining multiple identically constructed quarantine modules Q to configure and arrange a quarantine suite that is scalable to any size as shown in FIG. 9. Each individual quarantine module Q has a dedicated access airlock 32 for contamination-free entry and exit. A quarantine suite of such kind may be set up in any relatively large hall where a virus-free and cross-contamination free zone must be assured for each patient. This not only suppresses the propagation process but also helps to hasten the recovery process without constantly exposing the patient to newly introduced biocontaminants.

The quarantine suite may also supplemented and organized with accesses, service hatches, connecting corridors etc. with the doors, windows, locks, connections, ducts etc. known from the related art.

Consequently, the following advantages may be ascribed to the described quarantine system according to the invention:

The system can be erected very quickly, within a few minutes, in any location in the world, and is ready for operation immediately upon commissioning.

It offers maximum protection from cross-contaminations and any potential viral transfer which is to be avoided.

The system is sterilisable and washable.

After sterilisation or washing, the system can be packed in convenient, sterile packages, for example by welding in to gastight/sterile foil pouches, so that it is ready for use immediately after unpacking, and therefore can be stored in sterile conditions for long periods and is easy to keep sterile when transporting.

The system can be manufactured in advance very inexpensively.

Its very small package dimensions (collapsible) mean that larger storage spaces do not have to be set aside, storage can take up very little room.

Maximum protection for operating and service staff and doctors.

Maximum protection for quarantine patients from re-infection.

Inexpensive operation of the cleanliness-compatible quarantine system, with no complex gas, power or chemical supplies.

The media needed to care for the patient (power cables, data cables, hoses, etc.) can be introduced very quickly and simply through integrated, closable openings.

No complex disposal of materials contaminated with virus or biocontaminants is necessary with inexpensive, simple disposal as needed.

Reuse possible.

Low procurement costs.

Negligible operating costs (only electricity for ventilator unit and electricity for running the UVC sterilisation lamps) are necessary.

Operationally reliably application is achieved.

Preferred areas of use for the protection apparatus according to the solution are summarized as follows:

Cleanliness-compatible/hygiene (free from viruses/bacteria and other microorganisms) controlled areas such as are needed in the following application fields:

Aerospace, optics, life sciences (biochemistry, bioinformatics, biology, biomedicine, biophysics, bio- and genetic engineering, vaccination development, medicine (hospital, temporary hospital, hospital beds, intensive care units, operating theatres, doctors' surgeries, wards in health offices, airports, railway stations and conference halls, field research), medical engineering, pharmaceuticals and pharmacology, environmental management and environmental engineering), chemistry.

LIST OF REFERENCE SIGNS

1 First layer
2 Second layer
3 Spacer layer
4 Supporting structure/Spacer fabric
5 Production engineering unit 6 Room region
7 Environment, cleanroom
8, 8', 8" Flow unit
9 Fluid duct
10, 10', 10" substance flow
11 Ultrapure air
11' Virus-fee and biocontamination free air flow
12, 12' Discharge
13 Third layer
14 Fourth layer
15 Further spacer layer
16 Sensor
17 Evaluation and Control unit
18 Signal
19 Air stream component flowing into the room region through the first layer
20 Air stream component flowing into the environment through the second layer
21 Flow unit, preferably filter-ventilator unit
22 Sterile feed line
23 Outlet area
24 Discharge
25 Second flow unit, designed as filter-ventilator unit
26 Floor area
27 Persons subject to quarantine
28 Ventilator Unit
29, 29' UVC irradiation unit
30 Contaminated room air
31 Feed for technical gases
32 Access airlock
S Protective envelope
L Air
U Environment
Q Quarantine module

The invention claimed is:

1. An apparatus comprising:
a protective envelope enveloping and surrounding at least one room region which directly adjoins a floor area, the protective envelope separating the at least one room region from an environment surrounding the protective envelope;
at least two layers including a first layer and a second layer separated by a spacer layer that spaces the first and second layers apart, the spacer layer being traversed by flow in a longitudinal direction through the spacer layer;
at least one flow unit fluidically connected to the spacer layer;
the first layer is permeable to flow, is mounted closest to the at least one room region and has a permeability to flow in the range from 500 to 49,000 $m^3/m^2/h$, the first and second layers are formed from only at least one material for directly enclosing a clean room of ISO classes 1 to 9 according to DIN EN ISO 14644-1:2016-06;
that the protective envelope has an outlet area to which a sterilization unit is attached; and
the at least one flow unit has an internal pressure formed inside the spacer layer which is greater than an inner room pressure formed inside the at least one room region which is greater than an ambient pressure in the environment surrounding the protective envelope.

2. An apparatus according to claim 1, comprising:
a flow outlet from the at least one flow unit fluidically connected to the spacer layer and the protective envelope has an outlet fluidically connected to at least one flow inlet of the flow unit or a further flow unit.

3. An apparatus according to claim 2, comprising:
a sterilization unit located inside at least one of the at least one flow unit and along a flow path between the flow outlet of the at least one flow unit and the spacer layer and along a flow path between the outlet and the flow inlet of the at least one flow unit or a further flow unit.

4. An apparatus according to claim 1, wherein the sterilization unit includes a UVC light source for creating a virus-free and biocontamination free air flow.

5. An apparatus according to claim 1, wherein the second layer has a flow permeability in a range from 0 to 100 $m^3/m^2/h$.

6. An apparatus according to claim 1, comprising:
a third layer and a fourth layer which are separated by a further spacer layer, the third layer is connected to the second layer by a joint or the second layer and the third layer is a single part, the fourth layer is flow-permeable, and the further spacer layer is supported with a structure that spaces the third and fourth layers apart and is traversable by flow in the longitudinal direction of the third and fourth layers.

7. An apparatus according to claim 6, wherein at least one flow unit is fluidically connected to the further spacer layer.

8. An apparatus according to claim 6, wherein the first layer and the fourth layer comprise a material with identical material properties, the second layer and the third layer comprise a material with identical properties, and the spacer layer and the further spacer layer each have a supporting structure comprise a same material with identical material properties.

9. An apparatus according to claim 1, wherein the at least one flow unit provides overpressure and has a flow inlet connected to a gas reservoir, has an opening to an atmosphere surrounding the protective envelope for providing at least one of intake ambient air and a fluid connection to the at least one room region that is delimited by the protective envelope.

10. An apparatus according to claim 9, wherein the flow unit is a filter ventilator for producing air according to DIN EN ISO 14644-1:2016-06 from ambient air, and the fluidic connection between the flow outlet and the at least one room region or the spacer layer is a hollow duct comprising a material according to DIN EN ISO 14644-14:2017-01.

11. An apparatus according to claim 1, comprising:
at least one sensor attached to each of the first layer, the second layer and the spacer layer which the at least one sensor is selected to sense at least one of:
particulate contamination, molecular contamination or chemical contamination, temperature, pressure, humidity, flow, electrostatic sensor, and biocontaminants.

12. An apparatus according to claim 11, wherein the at least one sensor is connected to an evaluation, a control, or a regulator unit, which each generates at least one signal transmittable by at least one of a superordinate software and to at least one of the flow unit and to the evaluation, control and regulator unit.

13. An apparatus according to claim 1, wherein the at least the spacer layer has at least two areas with flow permeabilities in the longitudinal direction which differ from each other.

14. A use of the apparatus according claim 1, comprising:
creating or maintaining the at least one room region to have control cleanliness either inside or outside of the room region separated by the protective envelope.

15. A use of the apparatus according claim 2, comprising:
creating or maintaining the at least one room region to be control for cleanliness either inside or outside of the at least one room separated from the environment by the protective envelope.

16. A use of the apparatus according to claim 1, comprising making a facility by creating a room region free from viruses and cross-contamination to accommodate at least one of persons and objects which are subject to quarantine.

* * * * *